US006207130B1

(12) United States Patent
Kareiva et al.

(10) Patent No.: US 6,207,130 B1
(45) Date of Patent: Mar. 27, 2001

(54) METAL-EXCHANGED CARBOXYLATO-ALUMOXANES AND PROCESS OF MAKING METAL-DOPED ALUMINA

(75) Inventors: Aivaras Kareiva, Vilnius (LT); Chuansheng Bai, Clifton, NJ (US); Charles Jeffrey Harlan, New York, NY (US); D. Brent MacQueen, Golden, CO (US); Andrew R. Barron, Houston, TX (US); Ronald L. Cook, Lakewood, CO (US)

(73) Assignees: Rice University, Houston, TX (US); TDA Research, Inc., Wheat Ridge, CO (US)

( * ) Notice: Subject to any disclaimer, the term of this patent is extended or adjusted under 35 U.S.C. 154(b) by 0 days.

(21) Appl. No.: 09/058,587

(22) Filed: Apr. 10, 1998

Related U.S. Application Data

(60) Provisional application No. 60/043,860, filed on Apr. 11, 1997.

(51) Int. Cl.$^7$ .............................. C01F 7/02; C01F 17/00; C01F 15/00; C07F 5/00; C01G 23/00
(52) U.S. Cl. ..................... 423/600; 423/263; 423/252; 423/253; 423/594; 423/598; 423/599; 534/13; 534/16; 556/27; 556/179
(58) Field of Search ................... 534/13, 16; 556/27, 556/179; 423/600, 263, 252, 253, 594, 598, 599

(56) References Cited

U.S. PATENT DOCUMENTS

| | | | |
|---|---|---|---|
| 4,188,309 | * | 2/1980 | Volker et al. ........................ 423/213.5 |
| 5,013,798 | * | 5/1991 | Hoxmeier et al. ..................... 525/338 |
| 5,606,087 | * | 2/1997 | Roberg et al. ......................... 556/179 |
| 5,612,009 | * | 3/1997 | Fetzer et al. ......................... 423/239.1 |
| 5,902,891 | * | 5/1999 | Sangokoya et al. ................... 556/179 |

OTHER PUBLICATIONS

Apblett, A.W. et al. (1992) "From Minerals to Materials: A facile synthetic route to preceramic polymers for aluminum oxide" *Mat. Res. Soc. Symp. Proc.* 249:75–80.
Cai, G.–Z. et al.(1985), "Transmetalation of Tetranuclear Copper Complexes. 3. Effects of Ligands . . ." *Inorg. Chem.* 24:1701–1705.
Davies, G. et al. (1984), "Transmetallation Reactions of Tetranuclear Copper (II) Complexes. I. Crystal and Molecular Structures . . ." *Inorg. Chim. Acta.* 84:41–50.
Davies, G. et al. (1986), "Transmetalation of Tetranuclear Copper Complexes. 7. Spectral Evidence for the Substiochiometric Transmetalation of . . ." *Inorg. Chem.* 25:2269–2271.

El–Toukhy, A. et al. (1984), "Transmetalation Reactions of Tetranuclear Copper(II) Complexes. 2. Stiochiometry and Products of Reaction of [(DENC)CuCl]$_4$O$_2$ . . ." *J. Am. Chem. Soc.* 106:4596–4605.

Harlan, C.J. et al. (1997), "Yttrium–Doped Alumoxanes: A Chimie Douce Route to Y3A15012 (YAG) AND Y4A1209 (YAM)," *Adv. Mater.* 9(1):68–71.

Kareiva, A. et al. (1996) "Carboxylate–substituted alumoxanes as processable precursors to transition metal–aluminum and lanthanide–aluminum mixed–metal oxides: Atomic scale mixing via a new transmetalation reaction" *Chem. Mater.* 8(9):2331–2340.

Landry, C.C. et al. (1996) "From minerals to materials: Synthesis of alumoxanes from the reaction of boehmite with carboxylic acids" J. Mat. Chem. 5(2):331–341.

* cited by examiner

*Primary Examiner*—Steven Bos
(74) *Attorney, Agent, or Firm*—Greenlee, Winner and Sullivan, P.C.

(57) ABSTRACT

A method has been developed for the solution-based metal exchange of carboxylato-alumoxanes [Al(O)$_x$(OH)$_y$(O$_2$CR)$_z$]$_n$ with a wide range of metal cations. Metal-exchanged carboxylato-alumoxanes are new, particularly those in which about 10% to about 50% or more of the Al ions are exchanged for other metal ions. Additionally, the carboxylic acid ligands can be stripped from the boehmite core of metal-exchanged carboxylato-alumoxanes at low temperature leading to the formation of metal-exchanged boebmite particles. These new material phases can be used as intermediates for preparation of mixed metal aluminum oxide materials. Thermolysis of the metal-exchanged carboxylato-alumoxanes or metal-exchanged boehmite particles results in doped aluminas (M/Al$_2$O$_3$), binary (MAlO$_x$), ternary (MM'AlO$_x$) and even more complex metal aluminum oxide compounds, where M and M' are metal ions other than those of aluminum and are preferably those of Lanthanide metals or transition metals. The method allows preparation of pure phase materials as well as the preparation of metastable metal aluminum oxide phases. The carboxylato-alumoxanes are prepared by the reaction of boehmite (or pseudoboehmite) with carboxylic acids in a suitable solvent. Up to at least half of the aluminum cations in the boehmite lattice of the carboxylato-alumoxanes can be replaced by the reaction of metal acetylacetonates with the carboxylato-alumoxane in a suitable solvent. The metal exchange reaction can also be carried out by reaction with soluble metal salts. Reactions of boehmite with the metal acetylacetonates (or soluble metal salts) do not lead to the metal exchange reaction observed for the carboxylato-alumoxanes.

29 Claims, 1 Drawing Sheet

METAL-EXCHANGED CARBOXYLATO-ALUMOXANES AND PROCESS OF MAKING METAL-DOPED ALUMINA

CROSS-REFERENCE TO RELATED APPLICATIONS

Figure 1:
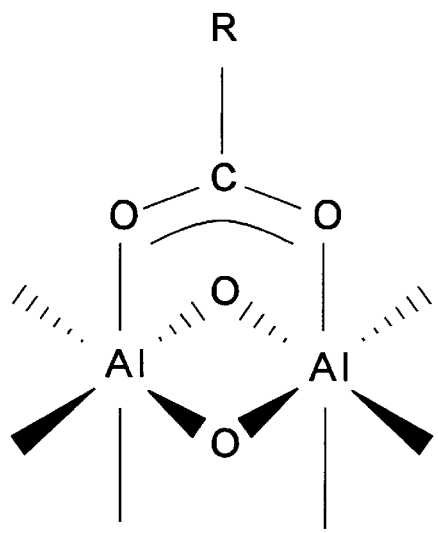
Figure 2:
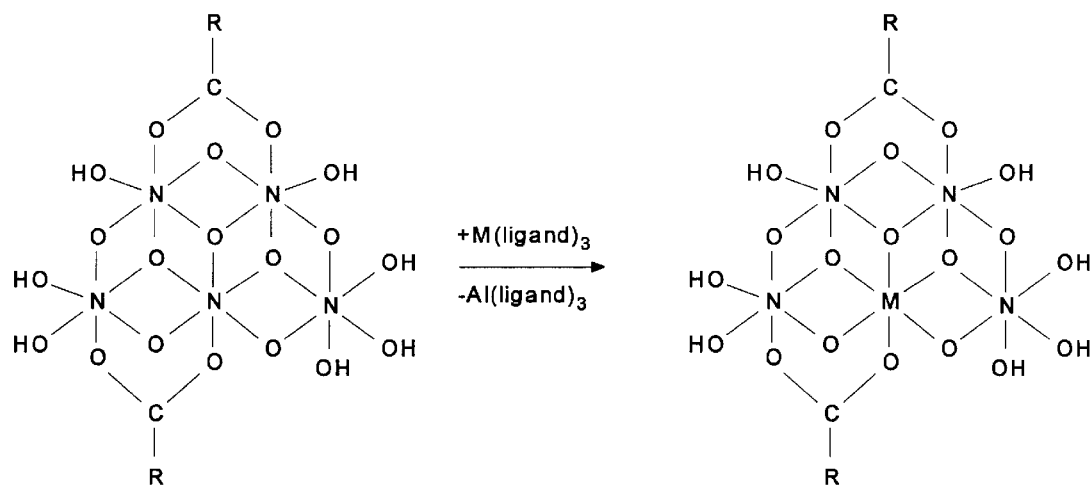

This application claims priority to U.S. provisional application Ser. No. 60/043,860, filed Apr. 11, 1997, pending which is incorporated in its entirety herein.

FIELD OF THE INVENTION

This invention relates generally to a method for making mixed metal aluminum oxide materials, by a metal exchange process that can be carried out in aqueous or organic solutions.

The method allows synthesis of metal-exchanged carboxylato-alumoxanes and metal-exchanged boehmite particles which can be converted to binary, ternary and more complex metal aluminum oxides upon thermal processing. Metal aluminum oxide structural classes that can be prepared by this method include, without limitation, spinels, garnets, perovskites, β-aluminas, and hexa-aluminates. The oxide structure that is obtained from the carboxylato-alumoxane depends on the metal used in the metal exchange reaction and the ratio of the metal to aluminum in the final product. For example exchanging yttrium into the alumoxane lattice to give a ratio of 3Y:5Al gives yttrium aluminum garnet, or exchanging magnesium into the alumoxane lattice to give a ratio of 1 Mg:1 Al gives magnesium aluminate spinel

BACKGROUND OF THE INVENTION

Binary and ternary metal aluminum oxides are technologically important classes of materials with applications in ceramics, optics, electronics, lasers and catalysis. $MgAl_2O_4$ (spinel) can be hot pressed into transparent windows with an exceptional infrared transmission range. $MgAl_2O_4$ is also used as refractory material for metal refining operations. $Y_3Al_{O12}$ (YAG) is widely used as a solid state laser material (Nd:YAG), and as a high energy phosphor (blue). YAG also has high temperature chemical stability and the highest creep resistance of any known oxide, leading to its evaluation as a promising fiber material for the preparation of ceramic composites. $LaAlO_3$ is being used as a substrate material for growth of thin film oxide superconductors. Mullite, an aluminosilicate, and cordierite (magnesium aluminosilicate) have exceptional high temperature shock resistance and chemical stability and the latter material is widely used in automotive catalytic converters.

The first requirement of a successful ceramic process is the availability of a good powder. Most of the advances in ceramic processing can be traced directly to the development of powders with controlled size and purity. Early ceramic processing used mineral based precursors that had a wide range of grain sizes and impurities. Ceramics formed from the mineral precursors often had glassy phases that reduced the performance of the ceramic. The development of solution based precipitation techniques that produced fine powders with well-defined particle size distributions and high purity significantly improved the fabrication of ceramic materials.

The traditional ceramic methods that are used to prepare binary (or more complex) aluminum oxides involves the physical mixing of the powders of the oxides (or oxide precursors), sintering at high temperatures for extended reaction times, grinding and re-sintering. High temperatures and long reaction times are necessary to overcome slow solid state diffusion since physical mixing is limited to the micron scale. The traditional ceramic approach provides a simple route to the preparation of powders, however the powders must then be formed into the desired shape by traditional processing methods (slip casting, extrusion, dry pressing etc.) and sintered to fabricate the shaped ceramic item.

In order to overcome the limitations of the traditional ceramic powder processing methods, chemical routes to the synthesis of complex aluminum oxide powders and ceramics are increasingly being adopted. The most widely employed methods are the sol-gel based techniques whose versatility, and potentially atomic level homogeneity, make them desirable approaches for the preparation of arrange of materials and forms. Sol-gel synthesis of alumina has traditionally been performed by the neutralization of a concentrated aluminum salt solution. However, the strong interactions between the freshly precipitated alumina gels and ions from the precursors solutions make it difficult to prepare the gels in pure form. To avoid this complication alumina gels are often prepared from the hydrolysis of aluminum alkoxides, $[Al(OR)_3]_n$, i.e.,

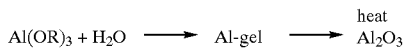

Although there can be significant advantages to the synthesis of metal aluminum oxides via the sol-gel route (such as preparation of small particles size and good homogeneity) there are a number of significant difficulties, including: long reaction times required (often greater than 24 hours), the addition of complexation agents that are necessary for inhibition of premature precipitation, careful pH control of the sol, low yields of gels from the alkoxide precursors, and the relative instability of the sols. The instability of the sols means that the sols must be prepared freshly, since storage results in precipitation. Furthermore, the fabrication of mixed metal aluminum oxides from alkoxides can be problematic, since the alkoxides can have different hydrolysis rates leading to phase segregation in the gels. Also the significant shrinkage of sol-gel based precursors leads to extensive cracking. For this reason fabrication of large ceramic objects via sol-gel routes is not generally feasible. In combination, these issues make sol-gel routes to monolithic aluminum oxides inconvenient for many applications.

It is desirable, therefore to identify materials and processes that can be used to prepare complex metal aluminum oxides starting with stable low cost precursors. The synthetic process should lend itself to the fabrication of a wide range of metal aluminum oxides with fine control over composition and particle size. The present invention provides a method of making metal aluminum oxides that provides these benefits and avoids many of the problems of prior art processes.

SUMMARY OF THE INVENTION

The present invention provides a solution-based metal-exchange process for synthesis of metal aluminum oxides, including binary, ternary and more complex metal aluminum oxides. The synthetic method is based on a metal-exchange reaction between metal acetylacetonates (or soluble metal salts) and carboxylato-alumoxanes that can be described by general formula:

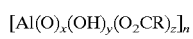

where x,y,z,n arc can be variable depending on the preparation method of the boehmite and the amount of the carboxylic acid used, and where R $CO_2^-$ is a monocarboxylate, where R is an organic group containing carbon with optional hetero-atom functional groups, and is preferably an alkyl, alkenyl, aromatic, haloalkyl, or haloalkenyl, haloaromatic group or an alkyl, alkenyl or aromatic ether group. These components are prepared by methods described in Landry et al. (1995), Apblett et al. (1992) and Kareiva et al. (1996). The composition of the carboxylato-alumoxanes varies dependent upon the starting materials employed and the details of the synthetic method employed as discussed in particular in Landry et al. (1995). The carboxylato-alumoxanes react to form metal-exchanged carboxylato-alumoxanes which can then be transformed to metal-exchanged boehmite particles and can be used as intermediates for preparation of mixed metal aluminum oxide materials. Thermolysis of the metal-exchanged carboxylato-alumoxanes or metal-exchanged boehmite particles results in doped aluminas ($M/Al_2O_3$), binary ($MAlO_x$), ternary ($MM'AlO_x$) and even more complex metal aluminum oxide compounds, where x has a value that renders the compound charge neutral, and M and M' are metal ions other than those of aluminum and are preferably those of lanthanide metals or transition metals. Boehmite is an aluminum oxyhydroxide (AlOOH) that is prepared by the hydrolysis of aluminum salts or aluminum alkoxides at temperatures above −80° C. and below −300° C. Its structure is that of a double layer of aluminum-oxygen octhedra whose layers are bound together by hydroxyls The ease of metal exchange into the carboxylato-alumoxanes depends upon the type of metal ion and its oxidation state. Certain metal ions, e.g., the lanthanide metals, exchange into the carboxylato-alumoxanes at room temperature in appropriate solvent. Other metal ions, e.g., those of $Ca^{2+}$, $Sr^{2+}$, $Co^{+2}$, $Ni^+$, $Mg^{2+}$, $Fe^{3+}$ and $Cu^{2+}$ are exchanged only slowly at room temperature and the exchange proceeds much faster with heating (typically to the boiling point of the solvent) and yet other metal ions, including $Bi^{+3}$, Cr ions and $Co^{+3}$ cannot be exchanged into carboxylato-alumoxanes by this method. Metal-exchange reactions of carboxylato-alumoxanes are preferably done in aqueous medium at ambient to near ambient (less than about 100° C.) temperatures.

The invention also provides the metal-exchanged carboxylato-alumoxanes produced by the inventive method and particularly metal-exchanged carboxylato-alumoxanes and metal aluminum oxides in which greater than about 10% of the aluminum ions are exchanged with another metal. The method of this invention is, however, particularly useful for the synthesis of metal-exchanged carboxylato-alumoxanes and metal aluminum oxides in which (1) greater than or equal to about 10% of the aluminum ions are exchanged with another metal, (2) greater than or equal to about 25% of the aluminum ions are exchanged with another metal, or (3) greater than or equal to about 50% of the aluminum ions are exchanged with another metal. Metal-exchanged carboxylato-alumoxanes and metal aluminum oxides generally include those in which about 10% to about 50% or more of the Al ions are exchanged for other metal ions.

Carboxylic acid ligands of metal-exchanged carboxylato-alumoxanes can be stripped from the boehmite core at low temperature leading to the formation of metal-exchanged boehmite particles. Thermolysis of the metal-exchanged carboxylato-alumoxanes or their metal-exchanged boehmite particles results in doped aluminas ($M_xAl_2O_3$, 0<x<1) binary ($M_wAl_yO_z$, w=1 to 5, y=1–12 z=1 to 18), ternary ($MM'AlO_x$, where M not equal to M') and even more complex metal aluminum oxide compounds, where M and M' are metal ions other than aluminum. M and M' independently of one another, can for example be ions of the alkali metals; the alkaline earth metals; the lanthanide metals: La, Ce, Pr, Nd, Pm, Sm, Eu, Gd, Tb, Dy, Ho, Er, Tm, Yb, and Lu as well as Y and Sc; the actinide metals (particularly Th and U); Group IIIB or Group IV B metals; or transition metals. As stated above, metal-doped aluminas generally include those in which about 10% to about 50% or more of the Al ions are exchanged for other metal ions.

Metal-exchanged carboxylate-alumoxane containing $Na^+$ or $K^+$ and their mixtures with $Li^+$ or $Mg^{2+}$ ions are specifically useful in the preparation of β"-alumina materials.

The method allows preparation of single phase materials as well as the preparation of metastable metal aluminum oxide phases. The carboxylato-alumoxanes are prepared by the reaction of boehmite (or pseudoboehmite) with carboxylic acids in a suitable solvent, the use of aqueous solvent media being preferred. Up to about half of the aluminum cations in the boehmite lattice of the carboxylato-alumoxanes can be replaced by the reaction of metal acetylacetonates with the carboxylato-alumoxane in a suitable solvent. The metal exchange reaction can also be carried out by reaction with soluble metal salts in a suitable solvent. The solvent can be dichloromethane or THF for example for alumoxanes soluble in organic solvents and water for alumoxanes soluble in water. Reactions of boehmite with the metal acetylacetonates (or soluble metal salts) do not lead to the metal exchange reaction observed for the carboxylato-alumoxanes.

DESCRIPTION OF THE INVENTION

This invention discloses a solution-based metal exchange process wherein metal cations can be exchanged for aluminum cations in the boehmite lattice of materials known as carboxylato-alumoxanes ($[Al(O)_x(OH)_y(O_2CR)_z]_n$) where x,y,z and n are variable depending on the synthesis conditions used to prepare the boehmite and the synthesis conditions and concentrations of the carboxylic acid used in the preparation of the alumoxane. The metal-exchanged carboxylato-alumoxanes are readily converted to doped aluminas ($M/Al_2O_3$), binary ($MAlO_x$), ternary ($MM'AlO_x$) (where x is a number that renders the compound charge neutral) and even more complex metal aluminum oxide compounds upon thermal processing. These conversions are done by application of sufficient heat to decompose the carboxylic acid and preferably to allow diffusion of the metal cations. Temperatures in the range of 325° C. to 600° C. are sufficient to decompose the alumoxane to give metal-exchanged $\gamma$-$Al_2O_3$. The temperatures required to cause diffusion of the cations to give the final oxide product depend on the cations exchanged and the structure to be formed. However, the temperature range for diffusion of the metal cations and formation of the end product is generally between 800° C. and 1700° C.

The carboxylato-alumoxanes are prepared by the reaction of boehmite or pseudoboehmite with carboxylic acids in a solvent such as xylenes for carboxylic acids that are highly hydrophobic (e.g. octanoic acid, lauric acid, steric acid, benzoic acid etc.) or water for carboxylic acids that are hydrophilic (hydroxyacetic acid, methoxy(ethoxyethoxy) acetic acid, 6-aminocaproic acid, 4-hydroxybenzoic acid, lactic acid, etc.) In some cases, heating is required for exchange. The boehmite (or pseudoboehmite) source can be a commercial boehmite product such as CATAPAL (A, B, C, D, or FI, Condea Vista Chemical Company) or boehmite prepared, for example, by the precipitation of aluminum nitrate with ammonium hydroxide followed by hydrothermal treatment at 200° C. for 24 hours or prepared by the hydrolysis of aluminum trialkoxides above 80° C. The carboxylic acid can be any monocarboxylic acid. Dicarboxylic acids cannot be used since they will cross-link the boehmite particles together leading to intractable products. The carboxylic acid can be aromatic or aliphatic, and can contain hetero-atom functional groups such as halogens, hydroxyls, amines, mercaptans, phosphines, etc. The metal exchange reaction does not appear to be sensitive to the type of monocarboxylic acid selected. However, the solution-based reaction does not occur in the absence of the carboxylic acids being bound to the surface of the boehmite particle.

The solution based metal-exchange reaction is carried out by dispersing or solubilizing a carboxylato-alumoxane in a solvent along with either a metal salt or metal acetylacetonate. The solvent is chosen to solubilize the carboxylato-alumoxane and can be an organic solvent such as dichloromethane or THF (tetrahydrofuran) for carboxylato-alumxoanes that are prepared using hydrophobic carboxylic acids (e.g. octanoic acid, lauric acid, steric acid, etc.) or water for carboxylato-alumoxanes prepared using hydrophilic carboxylic acids (e.g. hydroxyacetic, hydroxybenzoic, aminobutyric, etc.) The metal salt or the metal acetylacetonate is dispersed into the solvent with the carboxylato-alumoxane and the metal exchange reaction is carried out between about room temperature and the boiling point of the solvent. Solvents employed in this method include those that are mixtures of one or more components (e.g., aqueous alcohol). Successful metal exchange reactions of the carboxylato-alumoxanes have been carried out using boehmite to whose surface has chemically bound carboxylic acids as varied as hexanoic acid, dimethoxybenzoic acid, lauric acid, acetic acid, gluconic acid and methoxy (ethoxyethoxy)acetic acid have been bound. The carboxylic acid is believed to be attached through its oxygen atoms in a bridging mode to two aluminum cations. The metal exchange reaction depends primarily on the presence of a bound carboxylic acid and is independent of the nature of the carboxylic acid. Carboxylato-alumoxanes, where $RCO_2^-$ is hexanoate, dimethoxybenzoate and laurate, are soluble in organic solvents. Alumoxanes where $RCO_2^-$ is acetate, gluconate and methoxy (ethoxyethoxy)acetate, are soluble in water. Metal acetylacetonates, useful in this reaction, can be selected without limitation from the acetylacetonates of $Li^+$, $Na^+$, $K^+$, $Mg^{2+}$, $Ca^{2+}$, $Sr^{2+}$, $Ba^{2+}$, $Ti^{4+}$, $V^{3+}$, $Mn^{2+}$, $Fe^{2+}$, $Fe^{3+}$, $Co^{2+}$, $Ni^+$, $Cu^{2+}$, $Zn^{2+}$, $Ga^{3+}$, $Y^{3+}$, $Zr^{3+}$, $Nb^{3+}$, $Ag^+$, $Cd^{2+}$, $In^{3+}$, $Sn^{2+}$, $Hf^{3+}$, $Re^{3+}$, $Hg^{2+}$, $Pb^{2+}$, $La^{3+}$, $Ce^{3+}$, $Nd^{3+}$, $Pr^{3+}$, $Th^{4+}$, and $U^{4+}$ or mixtures thereof. In some cases, e.g., $UO_2(acac)_2$ and $VO_2(acac)_2$, metal oxide acetylacetonates can be used in the exchange reaction.

All metal acetylacetonate complexes are not equally reactive with the carboxylato-alumoxanes materials. In general, the lanthanides can be readily metal exchanged into the boehmite lattice of the carboxylato-alumoxanes using lanthanide acetylacetonates by stirring the two reactants at room temperature in a few hours in THF or dichloromethane. Metal exchange with other metal acetylacetonates (such as (cobalt (II) acetylacetonate or calcium acetylacetonate) requires heating (e.g., about 50° C.–about 150° C., dependent at least in part on the solvent being used) and longer reaction times. For some metal acetylacetonates no metal-exchange reaction is observed. These metal acetylacetonates include chromium (III) acetylacetonate, molybdenum (VI) oxide acetylacetonate and bismuth (III) acetylacetonate. The former two metals are expected to be substitutionally inert based on their electron configuration.

At room temperature or temperatures near ambient (room temperature to about 100° C.), stirring the metal acetylacetonate with the carboxylato-alumoxane in a solvent such as water (for hydrophilic alumoxanes) or THF, or dichloromethane (for hydrophobic alumoxanes) results in the formation of the metal exchanged alumoxane and the formation of $Al(acac)_3$.

For some metals, the metal exchange reaction can be carried out using metal salts that are not acetylacetonate complexes. For example, when water-soluble metal salts such as ammonium cerium nitrate ($[NH_4]_2[Ce(NO_3)_6]$ or ammonium cerate sulfate ($[NH_4]_2[Ce(SO_4)_4]$) or strontium nitrate or nickel nitrate or cadmium nitrate, are mixed in solution with the carboxylato-alumoxanes, the metal cations are exchanged for the aluminum cations in the boehmite lattice and $Al(H_2O)_6^{3+}$ is formed. Metal-exchange reactions of this invention can be carried out with nitrate, sulfate and acetate salts (e.g. nickel or cobalt acetates) of the following metals: $Li^+$, $Na^+$, $K^+$, $Mg^{2+}$, $Ca^{2+}$, $Sr^{2+}$, $Ba^{2+}$, $Ti^{4+}$, $V^{3+}$, $Mn^{2+}$, $Fe^{2+}$, $Fe^{3+}$, $Co^{2+}$, $Ni^+$, $Cu^{2+}$, $Zn^{2+}$, $Ga^{3+}$, $Y^{3+}$, $Zr^{4+}$, $Nb^{3+}$, $Ag^+$, $Cd^{2+}$, $In^{3+}$, $Sn^{2+}$, $Hf^{3+}$, $Re^{3+}$, $Hg^{2+}$, $Pb^{2+}$, $La^{3+}$, $Ce^{3+}$, $Nd^{3+}$, $Pr^{3+}$, $Th^{4+}$, and $U^{4+}$ or mixtures thereof.

In cases in which the exchange of multiple metal ions is desired, the metal exchange reaction of different metal ions can be carried out at the same time (using a mixture of appropriate starting metal salts or acetylacetonate complexes) or by sequential metal-exchange reactions. The ratios of the exchanged metal concentrations in the final product are determined by the ratios of the metal complexes used in the metal exchange reaction. For example to prepare $Zn_{0.5}Co_{0.5}AlO_4$, one would use a 1:1 molar ratio of zinc to cobalt acetylacetonate (or a 1:1 molar ratio of the nitates, sulfates or acetates). The ratio of $Zn^{2+}$ and $Co^{2+}$, to Al is chosen to be 0.5. to 1.0.

As noted in Kareiva et al. 1996, the Ce(III)-doped alumoxane-formed aluminum oxide, unlike other alumoxane-formed mixed metal oxides examined in that reference (see Table 1, therein), had a color distinct from materials made by the ceramic method. The cerium-doped metal oxide made by the alumoxane route was yellow compared to the white oxide prepared by the ceramic route. Also compared to the white oxide prepared by the ceramic route, the yellow Ce-doped oxide of this invention exhibited an ESR signal (a broad intense resonance at g=2.21) which is consistent with the presence of $Ce^{3+}$. The alumoxane route thus, in some cases, can prepare doped metal oxides that can not be prepared by the ceramic route. The ceramic route apparently gives Ce(IV)-doped oxide, while the alumoxane route gives a material that contains $Ce^{3+}$. $Ce^{4+}/Ce^{3+}$ has been proposed as the active species in supported combustion catalysts for diesel engines, thus stable-Ce(III)-doped alumina produced by the alumoxane route has potential for such catalyst applications. Mn-doped gamma alumina (~3 weight percent Mn) has been prepared by reaction of manganese acetylacetonate with carboxylato-alumoxanes to give a $Mn/\gamma-Al_2O_3$ support that is stable towards reaction with $Co_3O_4$. This allows preparation of high activity $Co_3O_4/Mn/\gamma-Al_2O_3$ oxidation catalysts. Thus a range of metal exchanged alumina catalysts and catalyst supports can be prepared by the used of metal exchanged carboxylato-alumoxane precursors.

Reaction of boehmite or pseudoboehmite with metal acetylacetonates or other soluble metal salts does not lead to the formation of metal-exchanged boelmite or pseudoboehmite materials. The presence of the bound carboxylic acid is necessary for the metal-exchange reaction to occur.

The carboxylic acid ligand can be stripped from the metal-exchanged carboxylato-alumoxane to give metal-exchanged boehmite particles. The carboxylic acid can be stripped from the carboxylato-alumoxane, for example, by treatment with aqueous hydrogen peroxide solutions and heating to 25–100° C. or by treatment with aqueous caustic solutions 3–6N KOH, 3–6NNaOH. These treatments result in a metal-exchanged boehmite particle that are free of the carboxylic acid attached to the surface of the carboxylic acid.

Using the metal acetylacetonate reagents and certain water-soluble nitrate, sulfate and acetate salts, a wide compositional range of mixed metal carboxylato-alumoxanes and mixed metal boehmite particles can be prepared. These mixed metal materials can then be thermally processed to provide a wide range of mixed metal aluminum oxide compositions that include but are not limited to $M_aM'_bAlO_3$ (a=0–1, b=0–1, a+b=1), $M_aM'_bAl_2O_4$(a=0–1, b=0–1, a+b=1), $(M_aM'_b)Al_5O_{12}$(a=0–3, b=0–3, a+b=3), $M_aM'_bAl_{11}O_{18}$ (a=0–1, b=0–1, a+b=1). Other compositions that include lattices possessing aluminum and oxygen with one or more non-aluminum cations can also be prepared by the metal-exchange reaction of this invention from carboxylato-alumoxane precursors.

Supporting evidence for the metal-exchange reaction of the carboxylato-alumoxanes from NMR and IR spectroscopy (Kareiva, et al. 1996) is presented below.

A detailed description of the metal exchange reaction (and characterization of the reaction) for the reaction of La(acac)$_3$ with hexanato-alumoxane follows. The doped carboxylato-alumoxane was prepared by mixing the carboxylato-alumoxane and La(acac), (where acac is acetylacetonate) in deuterated dichloromethane. The reaction of La(acac)$_3$ was complete within 2 hours. The removal of the solvent under vacuum, followed by washing with Et$_2$O gave the La exchanged—carboxylato-alumoxane in almost stoichiometric yield. The dopants are taken up into the alumoxane's lattice quantitatively. When the La:Al (lanthanum acetylacetonate to alumoxane) ratio is 1:11, the lanthanum hexaluminate is formed (LaAl$_{11}$O$_{18}$) and when the ratio of La:Al is 1:1, the lanthanum aluminum perovskite is formed (i.e. LaAlO$_3$).

In order to probe the maximum level of dopant incorporation the synthesis of the La-doped alumoxane was carried out. It was found that at least 50% of the aluminum cations could be replaced and thermolysis of the resulting material gave LaAlO$_3$.

The physical appearance and solubilities of the La-doped carboxylate-alumoxanes are similar to those of the parent alumoxanes, except for having a color related to that of the La-dopant (light yellow for lanthanum, other colors are observed for other lanthanum groupd dopants, e.g. light purple for neodynium, white for yttrium). As with the parent alumoxanes, the doped-alumoxanes exist as large "fluffy" agglomerates, 50–200 mm in size, with a particle size estimated from SEM to be less than 0.1 microns in diameter. The X-ray diffraction of the doped-alumoxanes are essentially indistinguishable from those of the parent alumoxane. The La:Al atomic ratios for the La-doped alumoxanes were determined by microprobe analysis and are close to the values expected based upon the reaction ratio.

The IR spectra of the parent (methoxy(ethoxyethoxy) acetato-alumoxanes contain bands at 1596–1586 and 1473–1466 cm$^{-1}$, consistent with a bridging mode of coordination (Formula 1) of the carboxylic acid to the boehmite core. In addition, all of the IR spectra show a broad absorption band at 3700–3400 cm$^{-1}$ consistent with the presence of an aluminum-bound hydroxide group. Upon addition of the La(acac)$_3$ complex there is a reduction in the intensity of the hydroxide resonances and a broadening of the carboxylate bands, however, there are no resonances assignable to the metal precursor complex.

Formula I

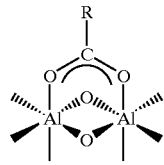

It has been previously demonstrated that the carboxylate alumoxanes (in common with all alumoxanes except those containing direct Al-C bonds) contain significant concentrations of acidic hydroxide groups (Landry et al. 1995). Metal acetylacetenoate complexes are known to be hydrolyzed to the appropriate oxide or hydroxide, and consequently have been widely used in sol-gel type synthesis. In view of this we expected that the reaction of the carboxylate alumoxane with M(acac)$_n$ (where n depends on the valence of M) should proceed as shown in the following equation:

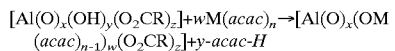

Although the hydroxide bands in the IR spectrum were altered upon reaction of the carboxylate alumoxane with M(acac)$_n$, there were no new bands assignable to the acac ligands, even when a large excess of the metal complex was employed.

To further study the reaction of the alumoxane precursors, solution NMR spectra were used to compare undoped and doped materials. The solution $^1$H and $^{13}$C NMR of the parent carboxylato-alumoxanes indicated a single environment for the bridging carboxylates. The reaction sequence between La(acac)$_3$ and a hexanato-alumoxane was then followed by multi-nuclear NMR. The $^{27}$Al NMR spectra of the alumoxanes before doping consist of a broad resonance at ca. 6 ppm indicative of aluminum in an octahedral AlO$_6$ coordination environment. The reaction of La(acac)$_3$ with hexanato-alumoxane in CDCl$_3$ was followed by $^1$H NMR. Upon mixing, the resonances due to La(acac)$_3$ diminish in intensity, and two new resonances are observed: d=5.48 (1H, s) and 1.99 (6H, s). These new signals are assigned to Al(acac)$_3$ by comparison with a commercial sample. Similarly, the $^{13}$C and $^{27}$Al NMR spectra of the reaction mixture confirm the presence of Al(acac)$_3$. If the reaction is carried out on a preparative scale, Al(acac)$_3$ can be isolated via crystallization.

Thus, the reaction of the La-acac complex with the alumoxane does not occur via reaction of the Al—OH groups but is believed to be the result of metal exchange and the leaching of aluminum from the boehmite core as shown by the reaction sequence below:

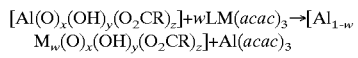

These results indicate that metal is incorporated into the boehmite-like lattice of the alumoxane. However, the exact ligand environment of the doping metal is uncertain, i.e., the extent to which the carboxylate ligands are involved in the coordination to the dopant metal is uncertain

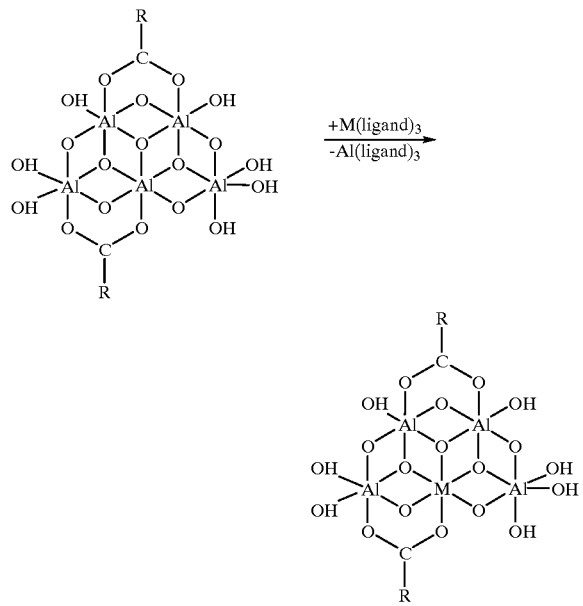

It thus appears that the metal metathesis reaction results from the direct reaction of the metal-acac complex with the carboxylate alumoxane. This is supported by the following: (a) n free acac-H is observed during the reaction, and (b) no Al(acac)$_3$ is formed from the reaction of alumoxanes with acac-H alone. Furthermore, carboxylic acids, for example methoxy(ethoxy—ethoxy)acetic acid (MEEA-H), do not react with La(acac)$_3$ to give acac-H. Since other carboxylato-alumoxanes undergo metal exchange with the metal acetylacetonates under the same conditions to give the same products, other carboxylic acids that have been used to prepare the alumoxanes should not react with La(acac)$_3$ to give acac-H and free La$^{3+}$. By extension, the metal-exchange should proceed similarly in other metal acetylacetonates. Since the boehmite starting material does not react with either M(acac), or acac-H, the carboxylate ligands on the alumoxane appear to assist metal metathesis. Evidence for this is observed from the $^{13}$C NMR spectrum of an alumoxane/La(acac)$_3$ reaction mixture. In addition to peaks due to the carboxylate a-carbons (O$_2$CR, d=185–174) and the carbonyl carbons of Al(acac)$_3$ (d=191.4), there is a peak at 191.1 ppm that can be assigned to La(acac)$_3$-MEEA-H, based upon a comparison with a genuine sample. The $^{13}$C NMR spectra of mixtures of La(acac)$_3$ with octanoic acid and tetraglyme also suggests that the interaction of La(acac)$_3$ with MEEA-H occurs via the carboxylate and not the polyether side chain. At the end of the reaction no free MEEA is seen in solution and is therefore still attached to the boehmite surface.

Metal exchange (transmetalation) reactions are well known for metal complexes and clusters. Transition metal complexes of monoanionic Schift bases have been shown by Davies and coworkers (Cai et al. 1985, Davies et al. 1984, Davies et al. 1986, El-Toukhy et al. 1984) to be stoichiometric transmetalating agents for the replacement of copper in various tetranuclear complexes. However, the low temperature solution-based metal metathesis between a mononuclear metal complex and a mineral particle (albeit solubilized), as in this invention, is believed unique. In Schift base transmetalations it is known that the driving force for the reaction is the formation of insoluble [CuL]$_x$ or highly stable CuL$_2$ co-products [where L=Schift base]. In the present case, the driving force for transmetalation between the carboxylate alumoxanes and the metal acetylacetenoate complexes is likely the formation of Al(acac)$_3$. However, in the case of soluble cerium salts, where the nitrate or sulfate salt are used, the driving force for reaction is either the formation of [Al(H$_2$O)]$^{3+}$, which is observed by $^{27}$Al NMR spectroscopy, or the binding of cerium into the alumoxane lattice.

Thermolysis of a carboxylato-alumoxane that has not been metal-exchanged gives γ-alumina, no matter what carboxylic acid is in the starting alumoxane. All of the metal-exchanged carboxylato-alumoxanes, up to a firing temperature of ~600–1100° C., give poorly crystalline metal doped γ-alumina structures. At higher temperatures (depending on the metal used and its concentration), the metal-exchanged carboxylato-alumoxanes transform to crystalline mixed metal oxides. For example, the use of ytrrium in a 3:5 Y:Al ratio gives Y$_3$Al$_5$O$_{12}$ at 1000° C. and the use of La in a 1:11 ratio gives LaAl$_{11}$O$_{18}$ at 1400° C. In contrast at lower temperatures materials prepared by conventional ceramic methods under similar conditions result in formation of dopant oxide and Al$_2$O$_3$ instead of the metal exchanged γ-alumina phase. For example, the thermolysis product of a physical mixture of [NH$_4$]$_2$[Ce(NO$_3$)$_6$] and boehmite shows a diffraction pattern consistent with a mixture of γ-alumina and CeO$_2$, while the ceramic obtained from the Ce-doped alumoxane is a Ce/γ-alumina (i.e. the cerium is incorporated into the alumina lattice).

Table 1 provides a summary of typical metal cations that can be exchanged into carboxylato-alumioxanes and the types of products that can be formed.

Like traditional sol-gel methodology, the use of carboxylate alumoxanes for the synthesis of aluminum-based oxide ceramics offers significant advantages over the ceramic method, including atomic scale mixing of metals and processability. However, unlike sol-gel synthesis the carboxylate alumoxanes are stable both in solution and the solid state. In addition, whereas the choice of solvents in sol-gel synthesis is limited, the solubility of the carboxylate alumoxanes is dependent on the identity of the carboxylic acid residue, which is almost unrestricted. The solubility of the alumoxanes may therefore be readily controlled so as to make them compatible with any co-reactants.

While these advantages are significant, the alumoxanes have further benefits with respect to large scale production of ternary and quaternary ceramics. The most dramatic is the simplicity of the alumoxane methodology. The alumoxane route is simple and can be halted and/or modified at any stage without significant detrimental effect on the products. A careful control of pH, the use of additives to inhibit precipitation, and slow concentration steps are not required, making the alumoxane route easier and quicker. A final benefit with respect to large scale processing is the relatively low cost of the alumoxane precursors and the production of singles phases after only a single firing.

The metal exchange reaction of this invention has a number of advantages over sol-gel approaches. The physical properties and chemistry of the metal-exchanged carboxylato alumoxanes can be readily controlled by the identity of the carboxylate group. For example use of a hydrophobic carboxylic acid such as octanoic acid gives an alumoxane soluble in dichloromethane and THF, use of hydroacetic acid gives alumoxanes that are soluble in water and the use carboxylic acids with bromo groups allows Grignard reagents to be used to modifiy the chemistry of the periphery of the carboxylato-alumoxane or the incorporation of amine functionalized carboxylic acids allows for amine chemistry to be carried out on the periphery of the carboxylato-alumxoane. Thus the presence of the carboxylic acids allows for metal ions to be incorporated into the surface lattice of the boehmite particles, allows the carboxylato-alumoxanes to be soluble in aqueous or non-aqueous solvents and permits chemical reactions to be carried out using functional groups that are part of the carboxylic acid. The ability to readily exchange metal cations into the surface lattice of the boehmite particles covered with the carboxylic acids allows the metal cations can be atomically dispersed into the surface crystal lattice of the boehmite particle. This allows extremely fine control of the homogeneity of doping procedure. In contrast to the sol-gel approaches, the carboxylato-alumoxanes are stable under a range of conditions thereby allowing processing under acidic and basic conditions. Furthermore, the boehmite and the carboxylic acids are both low in cost and low toxicity and can provide single phase products.

EXAMPLES

The following examples are presented to illustrate the ease and versatility of the approach and are not to be construed as in any way limiting the scope of the invention.

Example 1
Synthesis of Lanthanum-Exchanged Hexanato-Alumoxanes and the Subsequent Thermal Conversion to $LaAlO_3$ A 1:1 ratio of hexanato-alumoxane and $La(acac)_3$ were mixed in chloroform or THF at room temperature and stirred for one hour. The solvent does not need to be dry and the weight amount of solvent generally used is in the range of 10 to 20 times that of the alumoxane. Chloroform or THF solutions containing the hexanato-alumoxane in concentrations greater that 10 wt % tend to gel . The solvent was removed under vacuum and the resulting powder was washed with ether. Calcination of the resulting powder at 1,000° C. resulted in the formation of $LaAlO_3$. The XRD powder diffraction pattern of the resulting material showed it to be single phase $LaAlO_3$.

Example 2
Synthesis of Lanthanum-Exchanged Gluconato-Alumoxane and the Subsequent Thermal Conversion to $LaAlO_3$ A 1:11 molar ratio of $La(acac)_3$ and gluconato-alumoxane was mixed in water and stirred for two hours. The water was then removed under vacuum and the resulting powder washed with methanol. Calcination of the resulting powder at 1,400° C. resulted in the formation of $LaAl_{11}O_{18}$. The XRD powder diffraction pattern of the resulting material showed it to be single phase $LaAl_{11}O_{18}$.

Example 3
Synthesis of Yttrium Exchanged Methoxy(EthoxyEthoxy) Acetat-Alumoxane and the Subsequent Conversion to $Y_3Al_5O_{12}$ A 3:5 molar ratio of $Y(acac)_3$ and methoxy(ethoxyethoxy) acetatoalumoxane were mixed in water and stirred for two hours. The water was then removed under vacuum and the powder was washed with methanol. Calcination of the resulting powder at 1,000° C. resulted in the formation of $Y_3Al_5O_{12}$. The XRD powder diffraction pattern of the resulting material showed it to be single phase $Y_3Al_{O12}$.

Example 4
Synthesis of Manganese Cobalt Exchanged Gluconato-Alumoxane and the Subsequent Thermal Conversion to $Mn_{0.5}Co_{0.5}Al_2O_4$ A 0.5:0.5:2 molar ratio of $Co(acac)_2$, $Mn(acac)_2$ and gluconato-alumoxane are mixed in water and stirred for two hours at 75° C. The water was then removed under vacuum and the powder washed with methanol Calcination of the resulting powder at 1,000° C. resulted in the formation of $Mn_{0.5}Co_{0.5}Al_2O_4$. The XRD powder diffraction pattern of the resulting material showed it to be single phase $Mn_{0.5}Co_{0.5}Al_2O_4$.

Example 5
Synthesis of Mantanese-Exchanged Methoxy (EthoxyEthoxy)Acetato-Alumoxane and the Subsequent Thermal Conversion to $2\%Mn/Al_2O_3$ A 0.02:1 molar ratio of $Mn(acac)_3$ and methoxy (ethoxyethoxy)acetato-alumoxane were mixed in water and stirred for two hours at 75° C. The water was then removed under vacuum and the powders washed with methanol. Calcination of the resulting powder at 1,000° C. resulted in the formation of a $2\%Mn/Al_2O_3$ catalyst support material. The XRD powder diffraction pattern of the resulting material showed it to be single phase $2\%Mn/Al_2O_3$ material.

Example 6
Synthesis of Calcium-Exchanged Octanato-Alumoxane and the Subsequent Thermal Conversion to $CaAl_{12}O_{19}$ A 1:12 molar ratio of $Ca(acac)_2$ and octanato-alumoxane are mixed [DISSOLVED?] in THF and stirred for two hours at 50° C. The THF was then removed under vacuum and the powders washed with methanol. Calcination of the resulting powders at 1,400° C. resulted in the formation of $CaAl_{12}O_{19}$. The XRD powder diffraction pattern of the resulting material showed it to be single phase $CaAl_{12}O_{19}$.

Those of ordinary skill in the art will appreciate that procedures, techniques, and materials particularly starting materials, reagents, solvents, quantities and reaction conditions other than those specifically described herein can be readily used in the synthetic methods of this inventions without departing from the spirit and scope of this invention. All such alternative or functionally equivalent procedures, techniques, and materials are considered to be encompassed by this invention.

REFERENCES

Apblett, A. W.; C. C. Landry; M. R. Mason; A. R. Barron, *Mat. Res. Soc. Symp. Proc.*, 1992, 249, 73.

Cai, G. -Z.; Davies, G.; El-Toukhy, A.; Gilbert, T. R.; Henary, M. *Inorg. Chem.* 1985, 24, 1701

Davies, G.; El-Toukhy, A.; Onan, K. D.; Veidus, M., *Inorg. Chem. Acta.* 1984, 84, 41.

Davies, G.; El-Sayed, M. A.; El-Toukhy, A., *Inorg. Chem.* 1986, 25, 2269.

El-Toukhy, A.; Cai, G. -Z.; Davies, G.; Gilbert, T. R.; Onan, K. D.; Veidus, M., *J. Am. Chem. Soc.* 1984, 106, 4596.

Harlan, C. J.; A. Kareiva; D. B. MacQueen; R. Cook; A. R. Barron, *Adv. Mater.* 1997, 9(1), 68.

Kareiva, A.; C. J. Harlan; D. B. Mac(Queen; R. L. Cook; A. R. Barron, *Chemistry of Materials*, 1996, 8(9), 2331.

Landry, C. C.; N. Pappe; M. R. Mason; A. A. Apblett; A. N. Tyler; A. N. MacInnes; A. R. Barron, *J. Materials Chemistry*, 1996, 5(2), 331.

All of the references cited lherein are hereby incorporated by reference in their entirety herein.

TABLE 1

Typical Metal Cations that can be exchanged into alumoxanes and typical products formed by thermal treatment of the metal-exchanged alumoxane.

| Periodic Group | Metal Cations Exchanged | Examples of Types of Products Formed |
| --- | --- | --- |
| Group Ia | Li, Na, K, | Beta"-Alumina |
| Group II-a | Mg, Ca, Sr, Ba | hibonite, spinels |
| Group IIIb | Sc, Y, La, | hexa-aluminates, perovskites, garnets |
| Group Ivb | Ti, Zr, Hf | metal exchanged gamma-alumina |
| Group Vb | V, Nb | metal exchanged gamma-alumina |
| Group VIIb | Mn, Re | metal exchanged gamma-alumina, spinels |
| Group VIII | Fe, Ru, Co, Ni, Pd, Pt | metal exchanged gamma-alumina, spinels |
| Group Ib | Cu, Ag | metal exchanged gamma-alumina, spinels |
| Group II-b | Zn, Cd, Hg | metal exchanged gamma-alumina, spinels |
| Group IIIa | Ga, In | metal exchanged gamma-alumina, perovskites |
| Group Iva | Sn, Pb | metal exchanged gamma-alumina |
| Lanthanides | Ce, Pr, Nd, Sm, Eu, Gb, Tb, Dy, Er, Tb | hexa-aluminates, perovskites, garnets |
| Actinides | Th, U | metal exchanged gamma-alumina |

What is claimed is:

1. A metal-exchanged carboxylato-alumoxane.

2. The metal-exchanged carboxylato-alumoxane of claim 1 wherein 10% or more of the aluminum ions of the alumoxane are replaced with another metal ion or other metal ions.

3. The metal-exchanged carboxylato-alumoxane of claim 1 wherein from about 10% to about 50% of the aluminum ions of the alumoxane are replaced with another metal ion or other metal ions.

4. The metal-exchanged carboxylato-alumoxane of claim 1 wherein the exchanged metal is a metal ion selected from the group $Ca^{2+}$, $Sr^{2+}$, $Co^{2+}$, $Ni^+$, $Mg^{2+}$, $Fe^{3+}$ or $Cu^{2+}$ and mixtures thereof.

5. The metal-exchanged carboxylato-alumoxane of claim 1 wherein the exchanged metal is a metal selected from the group of the lanthanide metals.

6. The metal-exchanged carboxylato-alumoxane of claim 1 which comprises a monocarboxylic acid ligand $RCO_2$ wherein the R group is an alkyl group, alkene group or aromatic group optionally substituted with hetero-atom functional groups.

7. The metal-exchanged carboxylato-alumoxane of claim 1 which comprises a monocarboxylic acid ligand $RCO_2$ wherein the R group is an ether or halo-substituted alkyl, alkene or aromatic group.

8. The metal-exchanged carboxylato-alumoxane of claim 1 wherein the exchanged metal is an alkaline metal ion, an alkaline earth metal ion, a transition metal ion, an actinide metal ion, a Group III B metal ion, a Group IVB metal ion or mixtures thereof.

9. The metal-exchanged carboxylato-alumoxane of claim 1 wherein the exchanged metal is $Na^+$, $K^+$, or their mixtures with $Li^+$ or $Mg^{2+}$.

10. The metal-exchanged carboxylato-alumoxane of claim 1 which comprises two exchanged metal ions other than aluminum.

11. The metal-exchanged carboxylato-alumoxane of claim 1 comprising $Ce^{3+}$ or $Mn^{2+}$.

12. The metal-exchanged carboxylato-alumoxane of claim 1 which comprises a monocarboxylic acid ligand $RCO_2$ wherein the R group is an alkyl group, alkene group or aromatic group.

13. The metal-exchanged carboxylato-alumoxane of claim 1 wherein the exchanged metal is selected from the group $Li^+$, $Na^+$, $K^+$, $Mg^{2+}$, $Ca^{2+}$, $Sr^{2+}$, $Ba^{2+}$, $Ti^{4+}$, $V^{3+}$, $Mn^{2+}$, $Fe^{2+}$, $Fe^{3+}Co^{2+}$, $Ni^+$, $Cu^{2+}$, $Zn^{2+}$, $Ga^{3+}$, $Y^{3+}$, $Zr^{4+}$, $Nb^{3+}$, $Ag^+$, $Cd^{2+}$, $In^{3+}$, $Sn^{2+}$, $Hf^{3+}$, $Re^{3+}$, $Hg^{2+}$, $Pb^{2+}$, $La^{3+}$, $Ce^{3+}$, $Nd^{3+}$, $Pr^{3+}$, $Th^{4+}$, $U^{4+}$ and mixtures thereof.

14. The metal-exchanged carboxylato-alumoxane of claim 1 that is formed by metal exchange of a carboxylato-alumoxane with a metal acetylacetonate.

15. The metal-exchanged carboxylato-alumoxane of claim 1 that is formed by metal exchange of a carboxylato-alumoxane with a metal salt.

16. A method for making a metal-exchanged carboxylato alumoxane which comprises the steps of:

(a) combining a carboxylato-alumoxane wherein the carboxylic acid ligands are monocarboxylic acid ligands with a metal acetoacetonate or mixture of metal acetoacetonates solubilized or dispersed in a solvent to effect a metal-exchange reaction and (b) isolating said metal-exchanged carboxylato-alumoxane.

17. The method of claim 16 further comprising the step of preparing said carboxylato-alumoxane by reaction of boehmite or pseudoboehmite with a monocarboxylic acid.

18. The method of claim 16 wherein said carboxylato-alumoxane is water soluble and said combination is solubilized or dispersed in water.

19. The method of claim 16 wherein said carboxylato-alumoxane is soluble in dichloromethane or tetrahydrofuran and said combination is solubilized or dispersed in dichloromethane or tetrahydrofuran.

20. The method of claim 16 wherein said carboxylato-alumoxane comprises a ligand wherein said carboxylic acid ligand is acetate, gluconate, methoxy(ethoxyethoxy) acetate, hexanoate, dimethoxy benzoate, or laurate.

21. A method for preparing a metal-doped binary or tertiary alumina which comprises the step of heating a metal-exchanged carboxylato-alumoxane prepared by the method of claim 16 to strip the carboxylic acid ligands therefrom or form said alumina.

22. The method of claim 21 wherein the binary or tertiary alumina is a γ-alumina.

23. The method of claim 21 wherein the heating step is performed at temperatures ranging from 325° C. to 600° C.

24. The method of claim 21 wherein the heating step is performed at temperatures ranging from 800° C. to 1700° C.

25. The method of claim 21 wherein, in the metal-exchanged carboxylato-alumoxane, the exchanged metal is a metal ion selected from the group $Ca^{2+}$, $Sr^{2+}$, $Co^{2+}$, $Ni^+$, $Mg^{2+}$, $Fe^{3+}$, $Cu^{2+}$ and mixtures thereof.

26. The method of claim 21 wherein, in the metal-exchanged carboxylato-alumoxane, the exchanged metal is a lanthanide metal.

27. The method of claim 21 wherein, in the metal-exchanged carboxylato-alumoxane, the exchanged metal is an alkaline metal ion, an alkaline earth metal ion, a transition metal ion, an actinide metal ion, a Group III B metal ion, a Group IVB metal ion and mixtures thereof.

28. The method of claim 21 wherein the metal-doped alumina is selected from those having the compositions: $M_aM'_bAlO_3$, where a=0–1, b=0–1, and a+b=1; $M_aM'_bAl_2O_4$, where a=0–1, b=0–1, and a+b=1; $(M_aM'_b)Al_5O_{12}$, where a=0–3, b=0–3, and a+b=3; and $M_aM'_bAl_{11}O_{18}$, where a=0–1, b=0–1, and a+b=1 and wherein $M_a$ and $M'_b$ represent different metals, and are not aluminum.

29. The method of claim 16 further comprising the step of heating the combination of step (a) at or below the boiling point of the solvent.

* * * * *

UNITED STATES PATENT AND TRADEMARK OFFICE
CERTIFICATE OF CORRECTION

PATENT NO. : 6,207,130 B1
DATED : March 27, 2001
INVENTOR(S) : Kareiva et al.

It is certified that error appears in the above-identified patent and that said Letters Patent is hereby corrected as shown below:

At the 9th line of he Abstract, please replace "boebmite" with -- boehmite -- .

Column 1,
Line 31, please insert a period after "spinel".
Line 41, please replace "$Y_3Al_{o12}$" with -- $Y_3Al_5O_{12}$ --.

Column 2,
Line 16, please replace "of arange" with -- arrange -- .

Column 3,
Line 1, please delete "are".
Line 30, please insert a period after "hydroxyls".
Line 67, please replace "$M_xAl_yO_z$" with -- $M_wAl_yO_z$ -- .

Column 5,
Line 18, please replace "solvcnt" with -- solvent --.
Line 35, please delete "have been bound".
Line 65, please replace a "acetylacetonac" with -- acetylacetonate -- .

Column 9,
Line 2, pleace insert a period after "uncertain"
Line 31, please replace "n free" with -- no free -- .
Line 52, please replace "suggests" with -- suggest -- .

UNITED STATES PATENT AND TRADEMARK OFFICE
CERTIFICATE OF CORRECTION

PATENT NO.   : 6,207,130 B1
DATED        : March 27, 2001
INVENTOR(S)  : Kareiva et al.

It is certified that error appears in the above-identified patent and that said Letters Patent is hereby corrected as shown below:

Column 11,
Line 12, please replace "can" with -- to -- .
Line 54, please replace "Acetat-Alumoxane" with -- Acetato-Alumoxane -- .
Line 62, please replace "$Y_3Al_{012}$" as -- $Y_3Al_5O_{12}$ -- .

Column 12,
Line 4, please insert a period after "methanol".
Line 29, please delete "[DISSOLVED?]".

Signed and Sealed this

Eleventh Day of September, 2001

*Attest:*

NICHOLAS P. GODICI
*Attesting Officer*        *Acting Director of the United States Patent and Trademark Office*

UNITED STATES PATENT AND TRADEMARK OFFICE
CERTIFICATE OF CORRECTION

PATENT NO. : 6,207,130 B1
DATED : March 27, 2001
INVENTOR(S) : Kareiva et al.

Page 1 of 1

It is certified that error appears in the above-identified patent and that said Letters Patent is hereby corrected as shown below:

Column 1,
Line 4, please insert:

-- STATEMENT REGARDING FEDERALLY SPONSORED RESEARCH OR DEVELOPMENT
This work was supported by the Office of Naval Research, Contract No. N00014-95-C-0266. The United States government has certain rights in this invention. --

Signed and Sealed this

Sixth Day of November, 2001

Attest:

NICHOLAS P. GODICI
Attesting Officer
*Acting Director of the United States Patent and Trademark Office*

UNITED STATES PATENT AND TRADEMARK OFFICE
CERTIFICATE OF CORRECTION

PATENT NO. : 6,207,130 B1
DATED : March 27, 2001
INVENTOR(S) : Kareiva et al.

It is certified that error appears in the above-identified patent and that said Letters Patent is hereby corrected as shown below:

Abstract,
Line 9, please replace "boebmite" with -- boehmite --.

Column 1,
Line 31, please insert a period after "spinel".
Line 41, please replace "$Y_3Al_{012}$" with -- $Y_3Al_5O_{12}$ --.

Column 2,
Line 16, please replace "of arange" with -- arrange --.

Column 3,
Line 1, please delete "are".
Line 30, please insert a period after "hydroxyls".
Line 67, please replace "$M_xAl_yo_z$" with -- $M_wAl_yO_z$ --.

Column 5,
Line 18, please replace "solvcnt" with -- solvent --.
Line 35, please delete "have been bound".
Line 65, please replace a "acetylacetonac" with -- acetylacetonate --.

Column 9,
Line 2, please insert a period after "uncertain"
Line 31, please replace "n free" with no free --.
Line 52, please replace "suggests" with -- suggest --.

Column 11,
Line 12, please replace "can" with -- to --.
Line 54, please replace "Acetat-Alumoxane" with -- Acetato-Alumoxane --.
Line 62, please replace "$Y_3Al_{012}$" as -- $Y_3Al_5O_{12}$ --.

UNITED STATES PATENT AND TRADEMARK OFFICE
CERTIFICATE OF CORRECTION

PATENT NO. : 6,207,130 B1
DATED : March 27, 2001
INVENTOR(S) : Kareiva et al.

It is certified that error appears in the above-identified patent and that said Letters Patent is hereby corrected as shown below:

<u>Column 12,</u>
Line 4, please insert a period after "methanol".
Line 29, please delete "[DISSOLVED?]".

Signed and Sealed this

Twenty-seventh Day of November, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.    : 6,207,130 B1
DATED         : March 27, 2001
INVENTOR(S)   : Kareiva et al.

It is certified that error appears in the above-identified patent and that said Letters Patent is hereby corrected as shown below:

Title page,
Item [57], ABSTRACT,
Line 9, please replace "boebmite" with -- boehmite --.

Column 1,
Line 31, please insert a period after "spinel".
Line 41, please replace "$Y_3Al_{O12}$" with -- $Y_3Al_5O_{12}$ --.
Ine 65, please replace "involve" with -- involves --.

Column 2,
Line 16, please replace "a range" with -- arrange --.
Line 21, please replace "precursors" with -- precursor --.

Column 3,
Line 1, please delete "are".
Line 30, please insert a period after "hydroxyls".
Line 67, please replace "$M_xAl_yO_z$" with -- $M_wAl_yO_z$ --.

Column 5,
Line 18, please replace "solvcnt" with -- solvent --.
Line 35, please delete "have been bound".
Line 65, please replace "acetylacetonac" with -- acetylacetonate --.

Column 9,
Line 2, please insert a period after "uncertain".
Line 31, please replace "n free" with -- no free --.
Liune 52, please replace "suggests" with -- suggest --.

Column 11,
Line 12, please replace "can" with -- to --.
Line 54, please replace "Acetat-Alumoxane" with -- Acetato-Alumoxane --.
Line 62, please replace "$Y_3Al_{O12}$" with -- $Y_3Al_5O_{12}$ --.

UNITED STATES PATENT AND TRADEMARK OFFICE
CERTIFICATE OF CORRECTION

PATENT NO. : 6,207,130 B1
DATED : March 27, 2001
INVENTOR(S) : Kareiva et al.

It is certified that error appears in the above-identified patent and that said Letters Patent is hereby corrected as shown below:

Column 12,
Line 4, please insert a period after "methanol".
Line 29, please delete "[DISSOLVED?]".

Signed and Sealed this

Thirteenth Day of July, 2004

JON W. DUDAS
*Acting Director of the United States Patent and Trademark Office*